(12) United States Patent
Williams

(10) Patent No.: US 9,186,141 B2
(45) Date of Patent: Nov. 17, 2015

(54) CIRCULAR ANASTOMOSIS STAPLING APPARATUS UTILIZING A TWO STROKE FIRING SEQUENCE

(75) Inventor: Justin Williams, Naugatuck, CT (US)

(73) Assignee: Covidien LP, Mansfield, MA (US)

( * ) Notice: Subject to any disclaimer, the term of this patent is extended or adjusted under 35 U.S.C. 154(b) by 883 days.

(21) Appl. No.: 13/444,998

(22) Filed: Apr. 12, 2012

(65) Prior Publication Data

US 2013/0274771 A1    Oct. 17, 2013

(51) Int. Cl.
*A61B 17/04*    (2006.01)
*A61B 17/072*    (2006.01)
*A61B 17/115*    (2006.01)
*A61B 17/00*    (2006.01)

(52) U.S. Cl.
CPC ......... *A61B 17/072* (2013.01); *A61B 17/07207* (2013.01); *A61B 17/1155* (2013.01); *A61B 2017/00389* (2013.01); *A61B 2017/00393* (2013.01); *A61B 2017/00398* (2013.01); *A61B 2017/00464* (2013.01); *A61B 2017/00473* (2013.01); *A61B 2017/07278* (2013.01)

(58) Field of Classification Search
CPC ........... A61B 17/072; A61B 17/07207; A61B 17/1155; A61B 17/0293; A61B 2017/00389; A61B 2017/07278; A61B 2017/00398; A61B 2017/00464; A61B 2017/00473; A61B 2017/00393; A61B 2017/00477; A61B 2017/320052; A61B 2017/2933; A61B 2017/00314; A61B 2017/00353; A61B 2017/00367; A61B 2017/00371; A61B 2019/4857
USPC .......... 227/180.1, 175.1, 175.3, 179.1, 181.1, 227/182.1; 606/153
See application file for complete search history.

(56) References Cited

U.S. PATENT DOCUMENTS

| | | |
|---|---|---|
| 4,606,343 A | 8/1986 | Conta et al. |
| 5,205,459 A | 4/1993 | Brinkerhoff et al. |
| 5,271,543 A | 12/1993 | Grant et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,292,053 A | 3/1994 | Bilotti et al. |
| 5,312,024 A | 5/1994 | Grant et al. |
| 5,350,104 A | 9/1994 | Main et al. |
| 5,433,721 A | 7/1995 | Hooven et al. |
| 5,439,156 A | 8/1995 | Grant et al. |

(Continued)

FOREIGN PATENT DOCUMENTS

WO    WO 2009/039506 A1    3/2009

OTHER PUBLICATIONS

Extended European Search Report corresponding to EP 13163254.9, completed Jul. 1, 2013 and dated Jul. 10, 2013; (8 pp).

*Primary Examiner* — Stephen F Gerrity
*Assistant Examiner* — Joy N Sanders

(57) ABSTRACT

A circular anastomosis stapler is provided and includes a handle assembly having a firing trigger that is actuatable between a first firing stroke and a second firing stroke. A shell assembly includes a pusher assembly having a main pusher, a staple pusher and a knife pusher. A compressible member positioned between the main pusher and the knife pusher is movable between a first configuration for advancing the staple pusher through the first firing stroke to drive at least one staple from the shell assembly to staple tissue and a second configuration for advancing the knife pusher through the second firing stroke to drive a knife from the shell assembly to core the stapled tissue.

20 Claims, 12 Drawing Sheets

(56) References Cited

U.S. PATENT DOCUMENTS

| | | | |
|---|---|---|---|
| 5,445,644 A | 8/1995 | Pietrafitta et al. | |
| 5,609,285 A | 3/1997 | Grant et al. | |
| 5,632,433 A | 5/1997 | Grant et al. | |
| 5,839,639 A | 11/1998 | Sauer et al. | |
| 6,050,472 A | 4/2000 | Shibata | |
| 6,083,241 A | 7/2000 | Longo et al. | |
| 6,102,271 A | 8/2000 | Longo et al. | |
| 6,119,913 A | 9/2000 | Adams et al. | |
| 6,126,058 A | 10/2000 | Adams et al. | |
| 6,179,195 B1 | 1/2001 | Adams et al. | |
| 6,241,140 B1 | 6/2001 | Adams et al. | |
| 6,302,311 B1 | 10/2001 | Adams et al. | |
| 6,343,731 B1 | 2/2002 | Adams et al. | |
| 6,425,690 B1 * | 7/2002 | DeWachter | 384/583 |
| 6,443,973 B1 | 9/2002 | Whitman | |
| 6,478,210 B2 | 11/2002 | Adams et al. | |
| 6,517,565 B1 | 2/2003 | Whitman et al. | |
| 6,585,144 B2 | 7/2003 | Adams et al. | |
| 6,601,749 B2 | 8/2003 | Sullivan et al. | |
| 6,629,630 B2 | 10/2003 | Adams | |
| 6,695,198 B2 | 2/2004 | Adams et al. | |
| 6,716,233 B1 | 4/2004 | Whitman | |
| 6,805,273 B2 | 10/2004 | Bilotti et al. | |
| 6,817,508 B1 | 11/2004 | Racenet et al. | |
| 6,820,791 B2 | 11/2004 | Adams | |
| 6,827,246 B2 | 12/2004 | Sullivan et al. | |
| 6,840,423 B2 | 1/2005 | Adams et al. | |
| 6,866,178 B2 | 3/2005 | Adams et al. | |
| 6,874,669 B2 | 4/2005 | Adams et al. | |
| 6,981,941 B2 | 1/2006 | Whitman et al. | |
| 6,988,650 B2 | 1/2006 | Schwemberger et al. | |
| 7,032,798 B2 | 4/2006 | Whitman et al. | |
| 7,134,587 B2 | 11/2006 | Schwemberger et al. | |
| 7,147,140 B2 | 12/2006 | Wukusick et al. | |
| 7,207,472 B2 | 4/2007 | Wukusick et al. | |
| 7,404,508 B2 | 7/2008 | Smith et al. | |
| 7,410,086 B2 | 8/2008 | Ortiz et al. | |
| 7,419,080 B2 | 9/2008 | Smith et al. | |
| 7,546,939 B2 | 6/2009 | Adams et al. | |
| 7,694,864 B2 | 4/2010 | Okada et al. | |
| 7,784,663 B2 | 8/2010 | Shelton, IV | |
| 7,837,080 B2 | 11/2010 | Schwemberger | |
| 7,845,537 B2 | 12/2010 | Shelton, IV et al. | |
| 7,896,215 B2 | 3/2011 | Adams et al. | |
| 7,959,050 B2 | 6/2011 | Smith et al. | |
| 8,028,885 B2 | 10/2011 | Smith et al. | |
| 8,038,016 B2 | 10/2011 | Yuyama et al. | |
| 2003/0130677 A1 | 7/2003 | Whitman et al. | |
| 2004/0111081 A1 | 6/2004 | Whitman et al. | |
| 2005/0187576 A1 | 8/2005 | Whitman et al. | |
| 2009/0145947 A1 | 6/2009 | Scirica et al. | |
| 2009/0179063 A1 | 7/2009 | Milliman et al. | |
| 2011/0042443 A1 * | 2/2011 | Milliman et al. | 227/180.1 |
| 2011/0095070 A1 * | 4/2011 | Patel et al. | 227/181.1 |

* cited by examiner

CIRCULAR ANASTOMOSIS STAPLING APPARATUS UTILIZING A TWO STROKE FIRING SEQUENCE

BACKGROUND

1. Technical Field

The present disclosure relates generally to a circular anastomosis stapler. More specifically, the present disclosure relates to a circular anastomosis stapler having actuation stroke or strokes.

2. Background of Related Art

Anastomosis is the surgical joining of separate hollow organ sections so that the sections intercommunicate with each other. Typically, the anastomosis procedure follows surgery in which a diseased or defective section of hollow tissue is removed and the remaining end sections are to be joined. Depending on the desired anastomosis procedure, the end sections may be joined by either circular, end-to-side or side-to-side organ reconstruction methods.

In a circular anastomosis procedure, the two ends of the organ sections are joined by means of a stapling instrument, e.g., a circular anastomosis stapler, which drives a circular array of staples through the end sections of each organ section and simultaneously cores any overlapping tissue to free the tubular passage. Typically, these instruments include an elongated shaft having a handle portion at a proximal end to actuate the instrument and a staple holding component disposed at a distal end. An anvil assembly including an anvil rod with attached anvil head is mounted to the distal end. In operation, opposed end portions of the organs to be stapled are clamped between the anvil head and the staple holding component. The clamped tissue is stapled by driving one or more staples from the staple holding component so that the ends of the staples pass through the tissue and are deformed by the anvil head. The driving force is, typically, provided by a staple pusher. A cutting element, e.g., a cylindrical knife, is driven (simultaneously with the driving of the one or more staples into tissue) by a knife pusher to core the overlapping tissue to form an anastomosis ring therebetween. This type of firing sequence utilizes one linear drive motion to both fire the stapes and core the stapled tissue, e.g., utilizes a "single-stroke" firing or actuation sequence.

While circular anastomosis staplers that utilize a "single-stroke" firing or actuation sequence are capable of performing a circular anastomosis procedure, a circular anastomosis stapler that utilizes a single linear drive motion to provide a two-stroke firing sequence may prove useful in performing a circular anastomosis procedure.

SUMMARY

The present disclosure provides a circular anastomosis stapler. The circular anastomosis staler includes a handle assembly including a firing trigger that is actuatable between a first firing stroke and a second firing stroke. A shell assembly includes a main pusher, a staple pusher and a knife pusher. A compressible member is positioned between the main pusher and the knife pusher and is movable between a first configuration for advancing the staple pusher through the first firing stroke to drive at least one staple from the shell assembly to staple tissue and a second configuration for advancing the knife pusher through the second firing stroke to drive a knife from the shell assembly to core the stapled tissue.

The present disclosure provides a circular anastomosis stapler. The circular anastomosis staler includes a handle assembly including a firing trigger that is movable through a first firing stroke and a second firing stroke. A shell assembly includes a main pusher, a staple pusher and a knife pusher. The staple pusher is independently movable with respect to the knife pusher as the main pusher is moved through the first firing stroke. A compressible member is supported on the knife pusher and is selectively engageable with the main pusher when the main pusher is moved through the second firing stroke. The compressible member is transitionable between a compressed configuration for advancing the staple pusher through the first firing stroke to drive at least one staple from the shell assembly to staple tissue and an expanded configuration for advancing the knife pusher through the second firing stroke to drive a knife from the shell assembly to core the stapled tissue.

The present disclosure also provides a shell assembly that is configured for use with a circular anastomosis stapler. The shell assembly includes a main pusher, a staple pusher and a knife pusher. The staple pusher is independently movable with respect to the knife pusher as the main pusher is moved through the first firing stroke. A compressible member is supported on the knife pusher and is selectively engageable with the main pusher when the main pusher is moved through the second firing stroke. The compressible member is transitionable between a compressed configuration for advancing the staple pusher through the first firing stroke to drive at least one staple from the shell assembly to staple tissue and an expanded configuration for advancing the knife pusher through the second firing stroke to drive a knife from the shell assembly to core the stapled tissue.

BRIEF DESCRIPTION OF THE DRAWINGS

Various embodiments of the presently disclosed circular anastomosis stapler are disclosed herein with reference to the drawings wherein.

DETAILED DESCRIPTION OF EMBODIMENTS

Throughout this description, the term "proximal" will refer to the portion of the instrument closest to the operator and the term "distal" will refer to the portion of the instrument furthest from the operator.

Figure 1A:
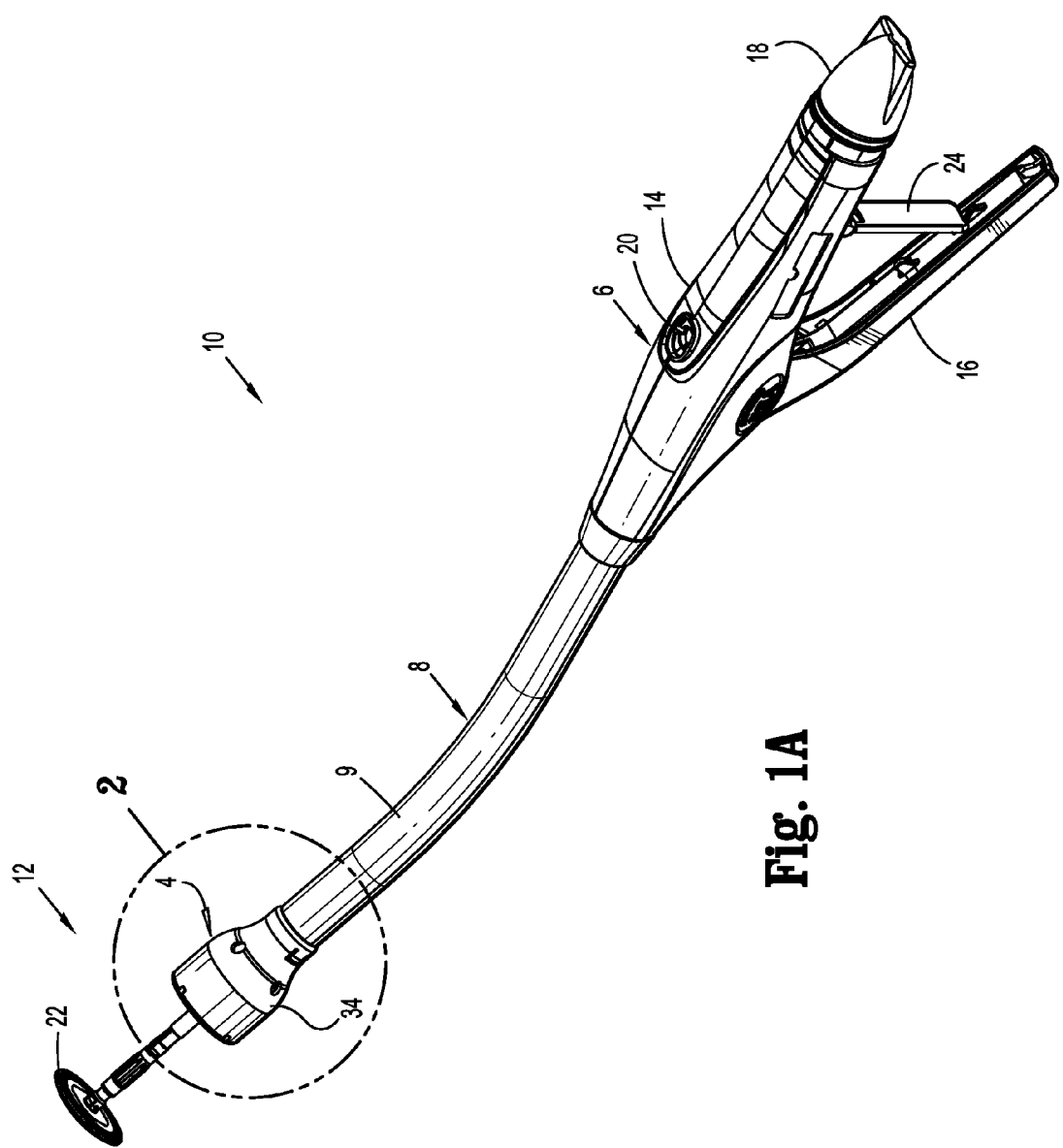
FIG. 1A is a side perspective view from the proximal end of a circular surgical stapling device that is configured for use with a shell assembly according to an embodiment of the present disclosure.

FIG. 1A illustrates a stapling apparatus, e.g., circular stapling device 10 that is configured for use with a shell assembly 4 in accordance with the present disclosure. Briefly, circular stapling device 10 includes a proximal handle assembly 6, an elongated body portion 8 including a curved elongated outer tube 9, and a distal head portion 12. Alternately, in some surgical procedures e.g., the treatment of hemorrhoids, it may be desirable to have a substantially straight central body portion and/or a flexible body portion (not explicitly shown). Handle assembly 6 includes a stationary handle 14, a firing trigger 16, a rotatable approximation knob 18 and an indicator 20. Trigger 16 is movable through a first firing or actuation stroke and a second firing or actuation stroke to move one or more components of the shell assembly 4 to staple and, subsequently, core (or sever) the stapled tissue. In certain embodiments, the device has a pair of movable triggers. In the illustrated embodiment a trigger lock 24 is provided to prevent inadvertent firing of the firing trigger 16. Alternatively, the handle assembly 6 may be provided without a trigger lock 24. Head portion 12 includes an anvil assembly 22 and the shell assembly 4. Anvil assembly 22 includes a plurality of staple forming depressions that are configured to form a corresponding plurality of staples (not explicitly shown) thereagainst when the anvil assembly 22 is in an approximated position with the shell assembly 4. The anvil assembly is movable toward and away from the shell assembly, which includes a staple cartridge assembly, by operation of an advancing mechanism so that rotation of the rotatable approximation knob 18 moves the anvil assembly.

Figure 1B:
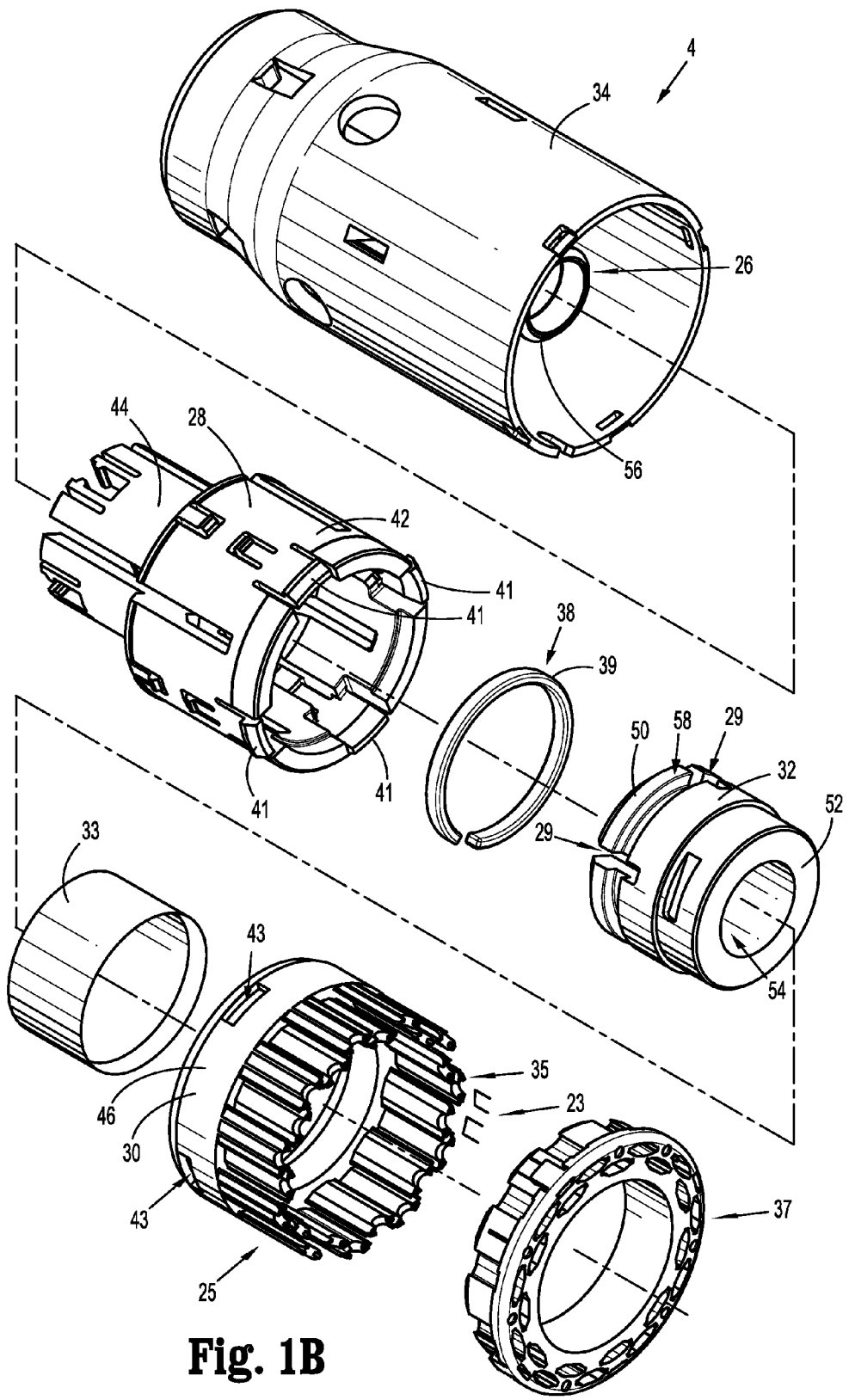
FIG. 1B is an exploded view illustrating components of the shell assembly separated.

The shell assembly 4 includes a staple cartridge assembly 25, which houses a plurality of staples 23 (FIG. 1B). In particular, cartridge assembly 25 includes an array of annular slots 37 that are configured to house a corresponding annular array of staples. In the illustrated embodiment, there are two annular arrays of slots 37 including an inner annular array of slots and an outer annular array of slots and corresponding annular arrays of staples. In certain embodiments, cartridge assembly 25 and anvil assembly 22 may include three annular arrays of staples and corresponding slots and staple forming depressions. Each of the staples 23 has a backspan and legs, and can be all the same, pre-formed size in the staple cartridge assembly. Alternatively, in any of the embodiments disclosed herein, the staples in one array of slots can have a different size than the staples in the other array or arrays of slots.

The slots 37 are aligned with a plurality of corresponding staple pushers 35. The staples may be made from any suitable biocompatible material including, but not limited, to surgical steel, shape memory alloys, polymeric materials, etc. Typically, the staples 23 are made from surgical steel or titanium. In certain embodiments, it may prove advantageous to have one or more annular array of staples, e.g., inner annular array of staples, made from one material and one or more annular array of staples, e.g., middle annular array of staples and/or outer annular array of staples, made from a different material.

It is contemplated that, in any of the embodiments disclosed herein, the staples have backspans that are bent or curved and that in other embodiments, the backspans of the staples have a straight configuration. It is also contemplated that in any of the embodiments disclosed herein, the staple cartridge assembly 25 can be a removable and replaceable unit.

Figure 10:
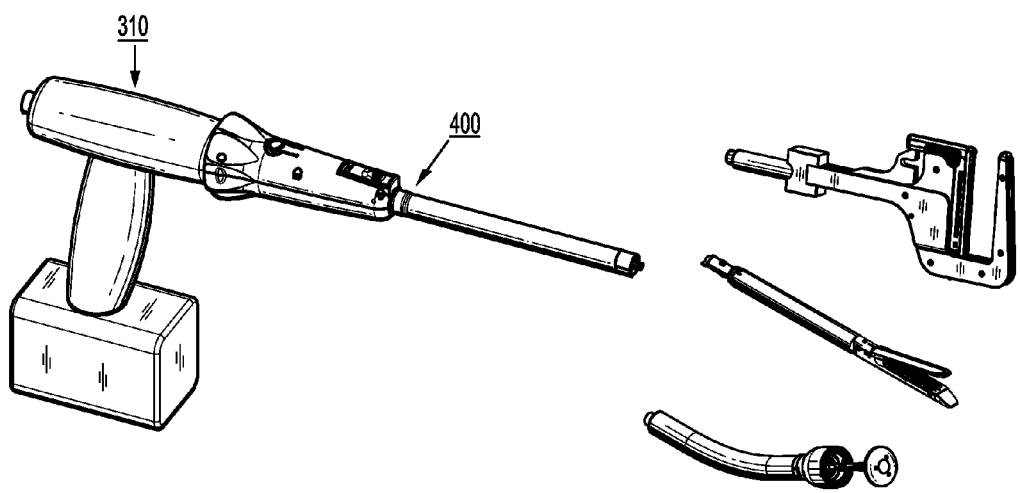
FIG. 10 is a perspective view of a powered surgical stapler including various replaceable heads.

It is also contemplated that the apparatus has a replaceable head including the cartridge assembly, anvil member and associated mechanisms. The stapling apparatus 10 can include the manually actuated handle assembly of FIG. 1A and as described above, or can include a powered actuator assembly having first and second drive members. For example, commonly owned U.S. Pat. No. 8,806,973, the entire disclosure of which is hereby incorporated by reference herein, discloses a surgical device 310 having a powered actuator assembly 400, see FIG. 10 for example. Such actuator assembly 400 can be powered by a motorized handle.

In certain embodiments, the operation of the staple pusher 30 can be utilized to vary the degree to which the staples 23 are deformed or crimped. For example, by approximating the anvil member more closely with the cartridge assembly, the staples 23 are crimped with a relatively smaller internal space and the tissue is compressed to a greater degree. Alternatively, the pusher member can be further advanced, further crimping or deforming the staples 23. Desirably, there is an indicator on the stapling apparatus handle assembly 6 that allows the surgeon to gauge the degree to which the staples will be crimped. The variable crimp can be used in any of the embodiments disclosed herein, including embodiments in which different sized (preformation) staples are used, same sized staples are used, bent or curved backspan staples are used, and/or bent or curved staple forming buckets are used.

It is also contemplated that the stapling apparatus can be configured to apply three rows of staples, and that the staples can have more than one bend in the backspan, or a curved backspan that is irregular (i.e., having more than one radius), in any of the embodiments disclosed herein.

The internal components of the shell assembly 4 are described with reference to FIGS. 1B and 2-6. Shell assembly 4 includes a shell body 34, a main pusher 28, a staple pusher 30 and a knife pusher 32 (FIG. 1B). The shell assembly 4 (and components operably associated therewith) may be made from any suitable material. In the illustrated embodiment, the shell assembly 4 includes shell body 34 that is made from one or more suitable metals, e.g., surgical steel, and pushers 28, 30 and 32 can be made from one or more suitable plastics that are relatively rigid.

Continuing with reference to FIGS. 1B and 2-6, shell assembly 4 includes an inner guide portion 26 that is configured to selectively receive a center rod (not shown) of the anvil assembly 22. Inner guide portion 26 is configured to support the main pusher 28 and knife pusher 32 thereon (FIGS. 2-6). A proximal portion 44 of the main pusher 28 is configured to slide along an exterior surface of the inner guide portion 26 when the firing trigger 16 is moved through the first and second firing strokes. Moreover, knife pusher 32 is configured to slide along the exterior surface of the inner guide portion 26 when the firing trigger 16 is moved through the second firing stroke.

One or more protuberances 27 (FIGS. 3-6) are provided on the inner guide portion 26 and are positioned at a medial portion thereof. The protuberances 27 are configured to selectively engage corresponding recesses 29 on the knife pusher 32 (FIGS. 1B and 3-6) when the main pusher 28 is in an initial configuration, see FIG. 3 for example. In this initial configuration, a compressible member 38 (FIGS. 1B and 2-6) that is coupled to the knife pusher 32 contacts a proximal surface of the protuberance 27 and an interior surface 21 of the main staple pusher 28, see FIG. 3 for example. Contact between the proximal surface of the protuberance 27 and interior surface 21 of the main staple pusher 28 maintains the knife pusher 32 in a substantially fixed orientation with respect to the inner guide portion 26 when the trigger 16 is moved through the first firing stroke. In particular, compressible member 38 is held in a compressed configuration by interior surface 21 and prevents knife pusher 32 from moving distally, described in greater detail below.

An annular recess 36 is provided along an outer surface of the inner guide member 26 and is located proximal to protuberances 27 (FIGS. 3-6). The function of the annular recess 36 is to allow the compressible member 38 to be compressed by the smaller inner diameter of the main pusher.

Figure 3:
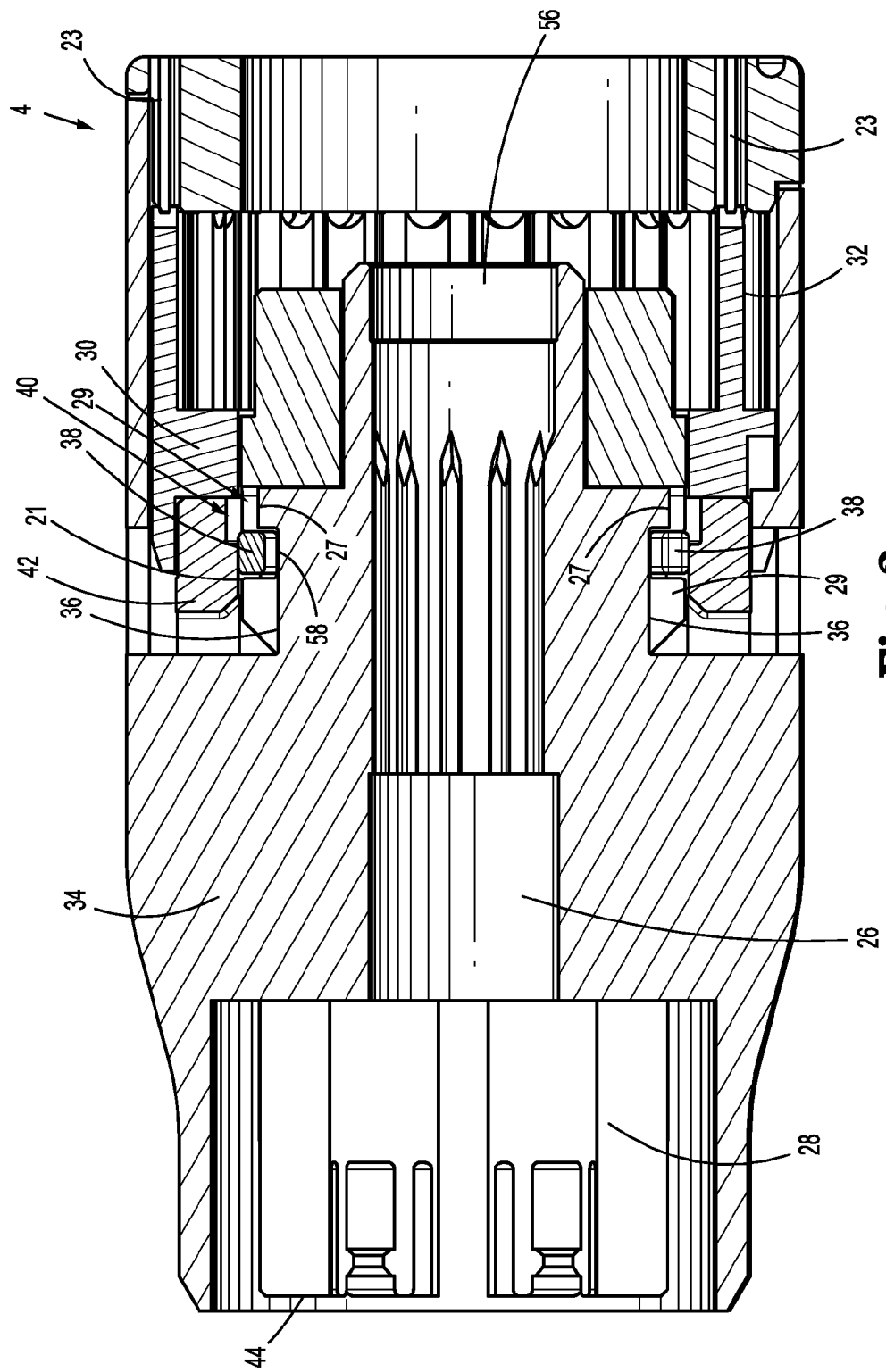
FIGS. 3-6 are side cross-sectional views illustrating positional relationships of the various components of the shell assembly during a two (2) stroke firing sequence of the circular stapling device shown in FIG. 1.
Figure 4:
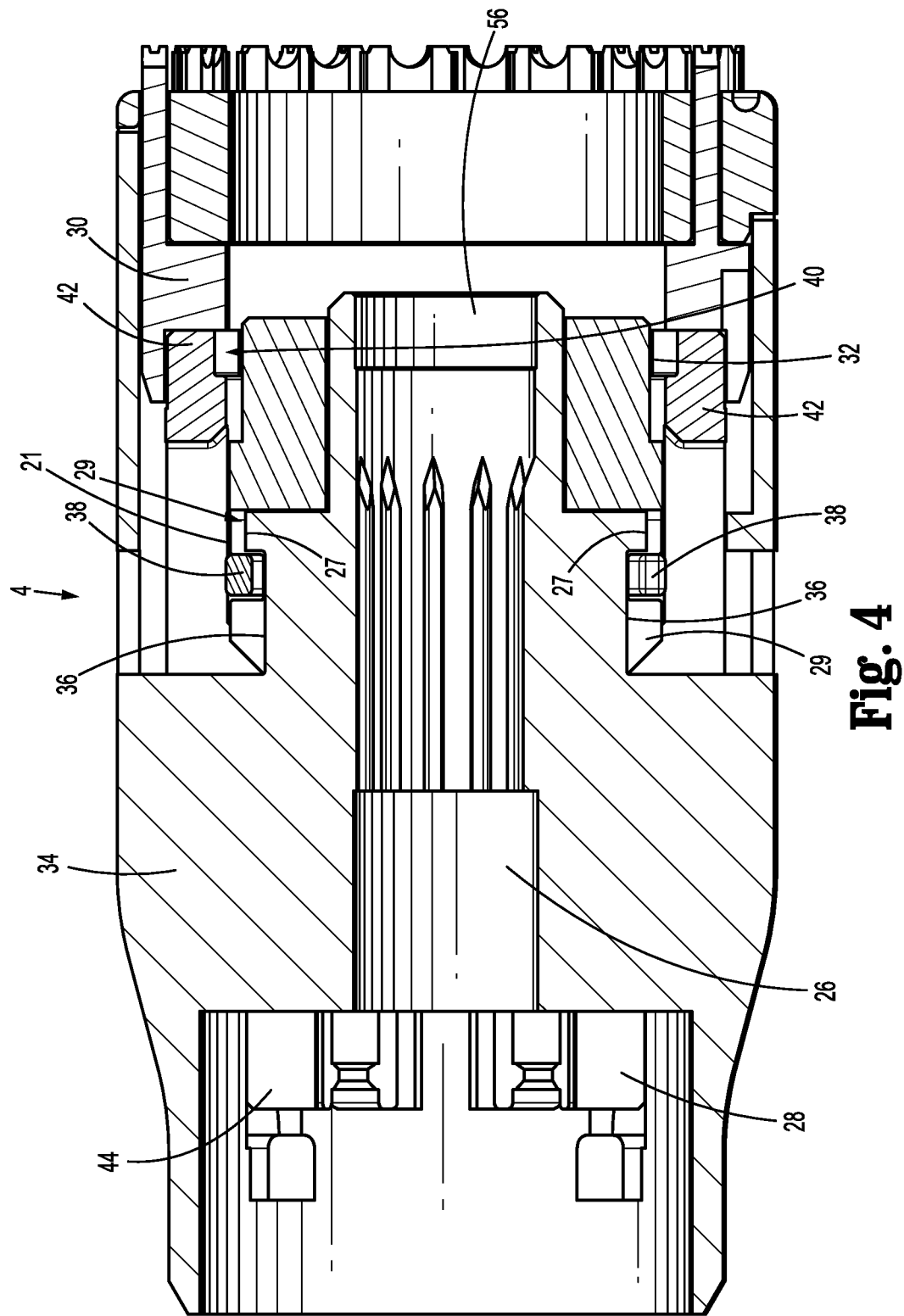

With reference again to FIG. 1B, the main pusher 28 includes respective proximal and distal portions 44, 42 and is configured to move the knife pusher 32 and staple pusher 30 as the firing trigger 16 is moved through the first and second firing strokes. In particular, distal portion 42 of the main pusher 28 is configured to slide along compressible member 38 during the first firing stroke to move the staple pusher 30 distally to drive one or more staples from the shell assembly 4 and against the staple forming depressions of the anvil assembly 22 (FIGS. 3-4). During the first firing stroke, the main pusher 28 and staple pusher 30 are movable with respect to the knife pusher 32 (FIGS. 3-4). Specifically, as the distal portion 42 of the main pusher 28 slides along the inner guide member 26 during the first firing stroke, the interior surface 21 of the distal portion 42 maintains the compressible member 38 in the first configuration, e.g., the compressed configuration (see FIGS. 3 and 4).

Figure 5:
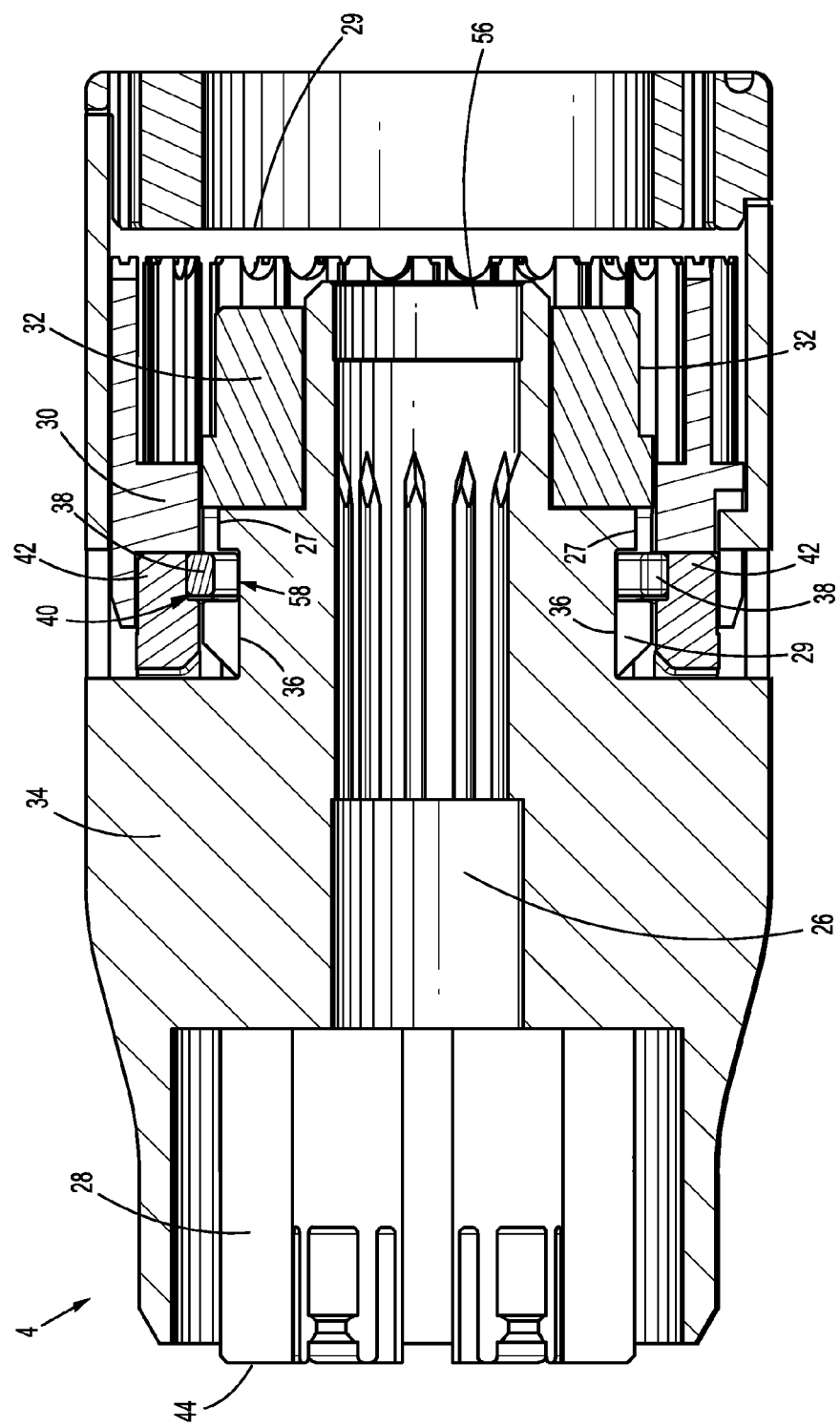
Figure 6:
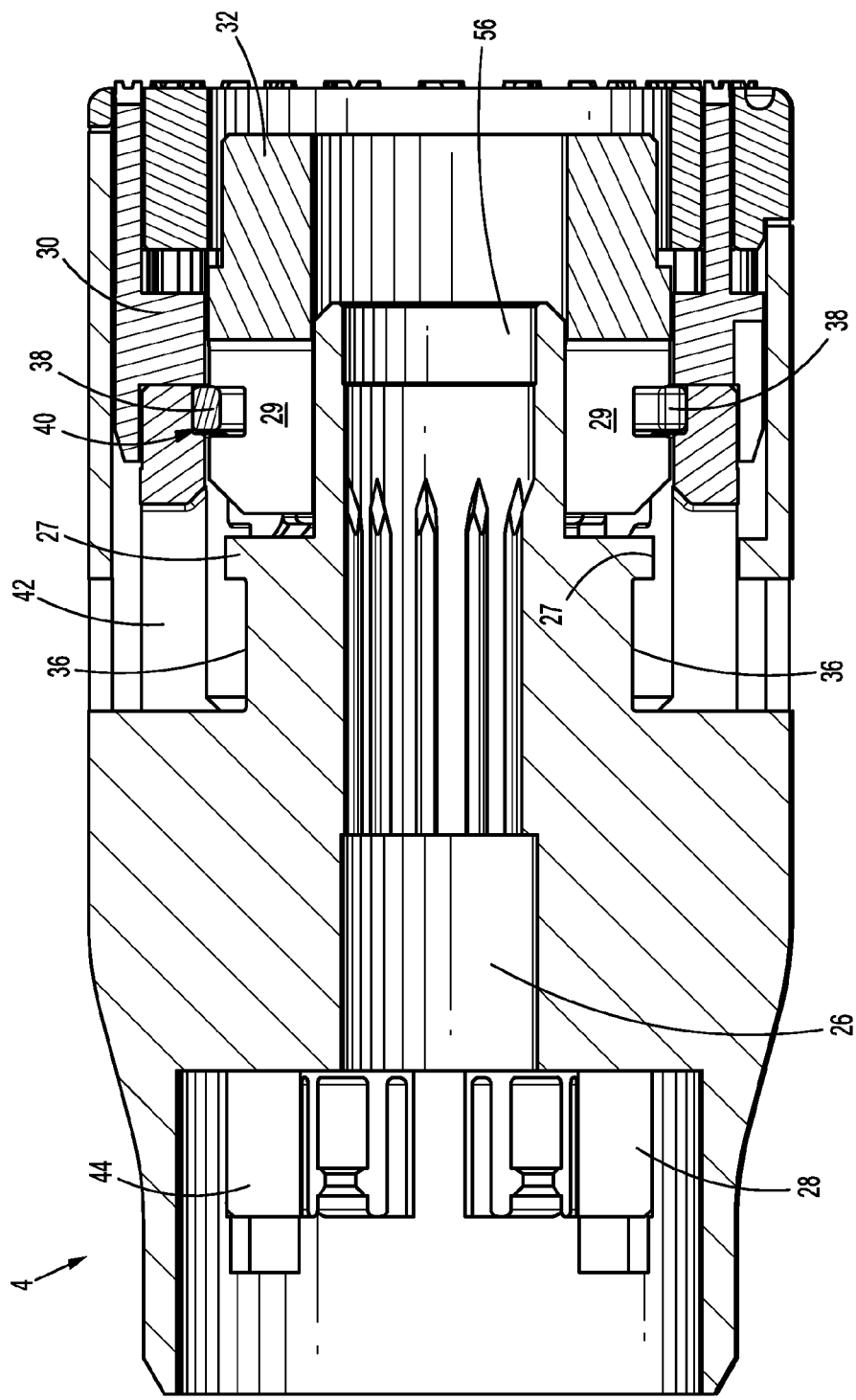

A notch 40 is defined at distal portion 42 of the main pusher 28 and is positioned distal to the compressible member 38 when the main pusher 28 is in the initial configuration, as best seen in FIG. 3. Subsequent to the first firing stroke, the main pusher 28 is configured to retract to a position that is proximal (FIG. 5) with respect to its initial position (FIG. 3). In this retracted position, the notch 40 is in vertical registration (FIG. 5) with the compressible member 38 to allow the compressible member 38 to move to its expanded configuration (FIGS. 5 and 6). The main pusher 28 is configured to slide over the inner guide member 26 along with the compressible member 38 during the second firing stroke to move the staple pusher 30 and the knife pusher 32 to drive a knife 33 from the shell assembly 4 to core the stapled tissue.

Proximal portion 44 of the main pusher 28 is configured to engage a pusher link (not explicitly shown) of the circular anastomosis stapler 2. In particular, as the firing trigger 16 is moved through the first firing stroke, the pusher link moves the main pusher 28 distally to engage the staple pusher 30 (FIGS. 3 and 4). Moreover, as the pusher link is moved through the second firing stroke, the pusher link moves the main pusher 28 distally to engage both the staple pusher 30 and the knife pusher 32 (FIGS. 5 and 6).

Figure 2:
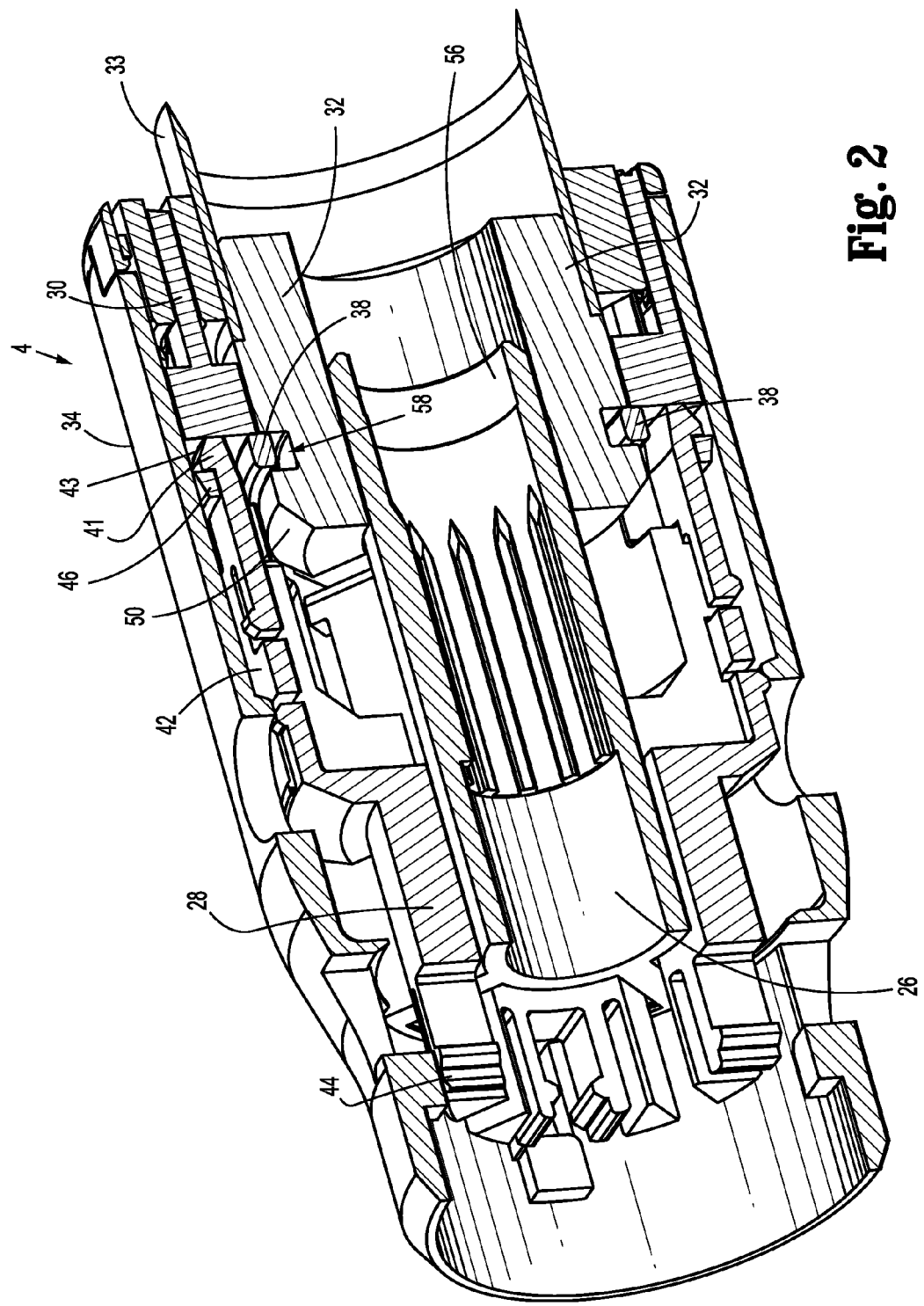
FIG. 2 is an enlarged view of the indicated area of detail illustrating in a cross-sectional isometric view the shell assembly shown in FIG. 1 with a portion of the shell assembly omitted.

Distal portion 42 of the main pusher 28 is proportioned to substantially surround the knife pusher 32 therein when the main pusher 28 is in its initial retracted position, see FIGS. 3 and 4. The distal portion 42 is configured to engage a proximal end 46 of the staple pusher 30 to move the staple pusher 30 distally through the first and second firing strokes (FIG. 2). In the embodiment illustrated in FIGS. 1B and 2-6, for example, one or more fingers 41 (FIGS. 1B and 2) are positioned along the distal portion 42 of the main pusher 28 and are configured to engage one or more corresponding slots 43 positioned at a proximal end of the staple pusher 30 (FIGS. 1B and 2).

A distal end of the staple pusher 30 includes a plurality of staple pushers 35 (FIG. 1B) configured to support the plurality of staples 23 thereon to drive the staples 23 through corresponding slots 37 (FIG. 1B) and against corresponding staple forming depressions of the anvil assembly 22.

Figure 1C:
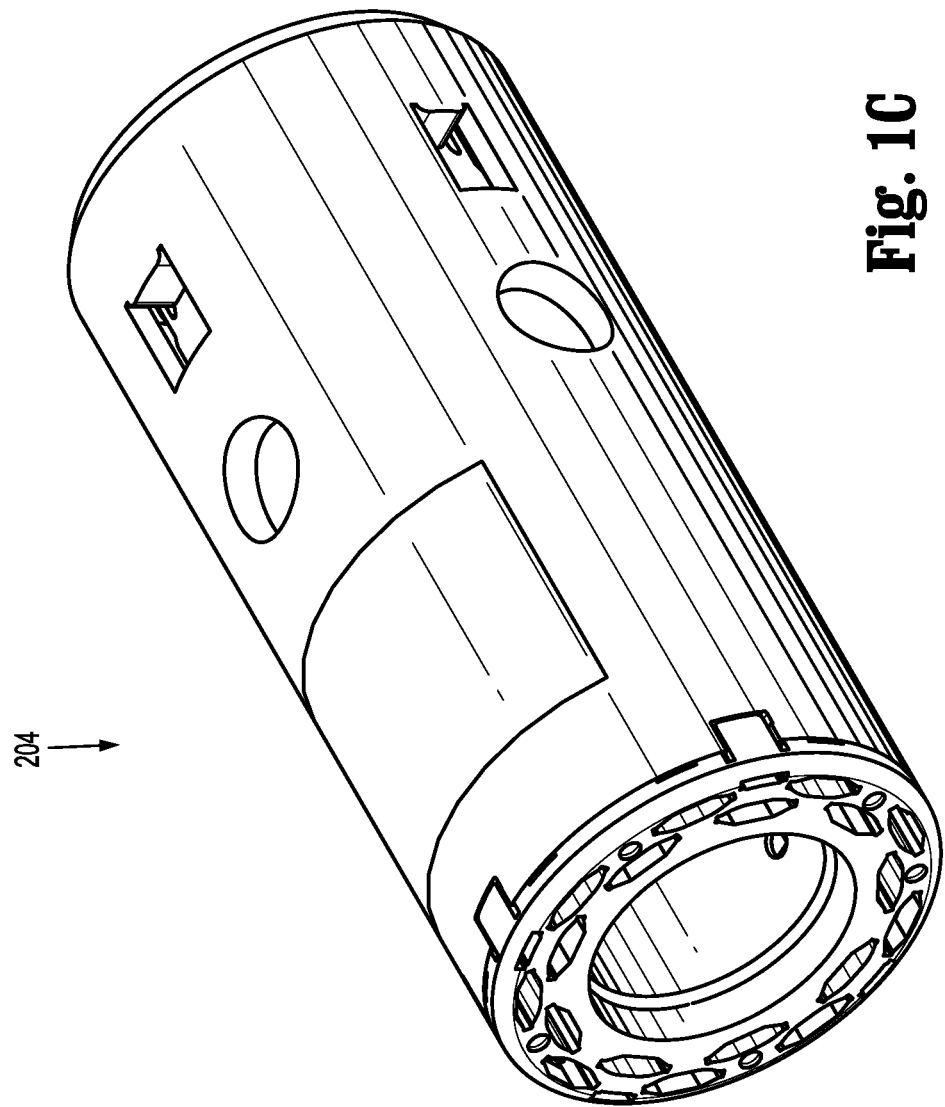
FIG. 1C is a perspective view of a shell assembly according to another embodiment of the present disclosure.

Knife pusher 32 includes a proximal end 50 and a distal end 52 (FIGS. 1B and 2). An opening 54 extends through the knife pusher 32 and is configured to receive a distal portion 56 of the inner guide portion 26 (FIGS. 1B-2). An annular recess 58 (FIGS. 1B, 2 and 5) that is configured to support the compressible member 38 therein extends along an outer circumferential surface of the knife pusher 32 adjacent the proximal end 50. The annular recess 58 is configured to allow the compressible member 38 to move between the first and second configurations as the main pusher 28 is moved from its initial position to its retracted position, see FIGS. 4 and 5, for example.

The compressible member 38 can be configured to have a generally circular shape with an opened-loop configuration that allows the member 38 to be compressed. In other embodiments, however, compressible member 38 may have a generally circular shape with a closed-loop configuration. Compressible member 38 is substantially resilient to facilitate moving between the first and second configurations (or transitioning between a compressed configuration to an expanded configuration). In the illustrated embodiment, the compressible member 38 is in the form of a compressible snap-ring 39 (FIG. 1B) that is seated within the annular recess 58. Compressible member 38 may be made from any suitable material, e.g., plastic, rubber, etc. Other compressible members can be used, such as various types of springs including a coil spring or garter spring. Such springs can be made of metal, plastic, or both, or any other suitable material.

In use, the anvil assembly 22 and shell assembly 4 of the circular anastomosis stapler 10 (FIG. 1A) are positioned within separate hollow organ sections to join these sections. The main pusher 28 is in its initial position (FIG. 3). The firing trigger 16 (FIG. 1A) is moved through a first firing stroke to fire the staple(s) of the circular anastomosis stapler. As the firing trigger 16 is moved through the first firing stroke, the main pusher 28 and the staple pusher 30 are moved distally. As the main pusher 28 moves distally, the interior surface 21 slides along the compressible member 38 thus maintaining the compressible member 38 in the first condition, i.e., the compressed configuration (FIGS. 3 and 4). The compressible member 38 being seated within the annular recess 58 of the knife pusher 32 and in contact with the proximal surface of the protuberance 27 and the interior surface 21 maintains the knife pusher 32 in a substantially fixed orientation while the main pusher 28 and staple pusher 30 are moved distally.

After the staple pusher 30 has driven the staple(s) from the shell assembly 4 and against the corresponding depression(s) in the anvil assembly to form the staple(s), the main pusher 28 including the staple pusher 30 are moved proximally to a retracted position. In this retracted position, the notch 40 is positioned in vertical registration with respect to the compressible member 38, which allows the compressible member 38 to move to its second configuration, i.e., its expanded configuration (FIGS. 5 and 6). In the expanded configuration, the compressible member 38 engages the notch 40 and maintains engagement with the annular recess 58 of the knife pusher 32.

To core the stapled tissue, the firing trigger 16 is moved through a second firing stroke. The second firing stroke moves the main pusher 28 that is now engaged with the compressible member 38 and, thus, the knife pusher 32 (FIGS. 5 and 6), which, in turn moves the knife pusher 32 and the knife 33 distally to core the stapled tissue.

Unlike conventional circular anastomosis staplers, the circular anastomosis stapler 10 in accordance with the instant disclosure includes a shell assembly 4 that utilizes a single linear drive motion to first fire the staple(s) to staple tissue and, subsequently, drive the knife 33 to core the stapled tissue. As can be appreciated, the force required to actuate the trigger 16 to individually drive the staples 23 and the knife 33 is less than a force that would be required to actuate the trigger 16 to simultaneously drive the staples 23 and the knife 33. Driving the knife 33 separately also tends to avoid poor staple alignment that may result when the knife 33 contacts the tissue first, pulling on the tissue during firing.

From the foregoing and with reference to the various figure drawings, those skilled in the art will appreciate that certain modifications can also be made to the present disclosure without departing from the scope of the same. For example, while the main pusher 28 has been described including one or more fingers 41 that are configured to engage one or more corresponding slots 43 to couple the main pusher 28 to the staple pusher 30, other coupling methods can be utilized. For example, and with reference to FIGS. 7-9, an alternate embodiment of the main pusher 28 and staple pusher 30 are illustrated with regards to a shell assembly 104. The other components can be as discussed above. In this instance, main pusher 128 includes one or more notches 141 that are configured to engage one or more corresponding protuberances 143 on the staple pusher 130 to couple the main pusher 128 to the staple pusher 130.

Figure 7:
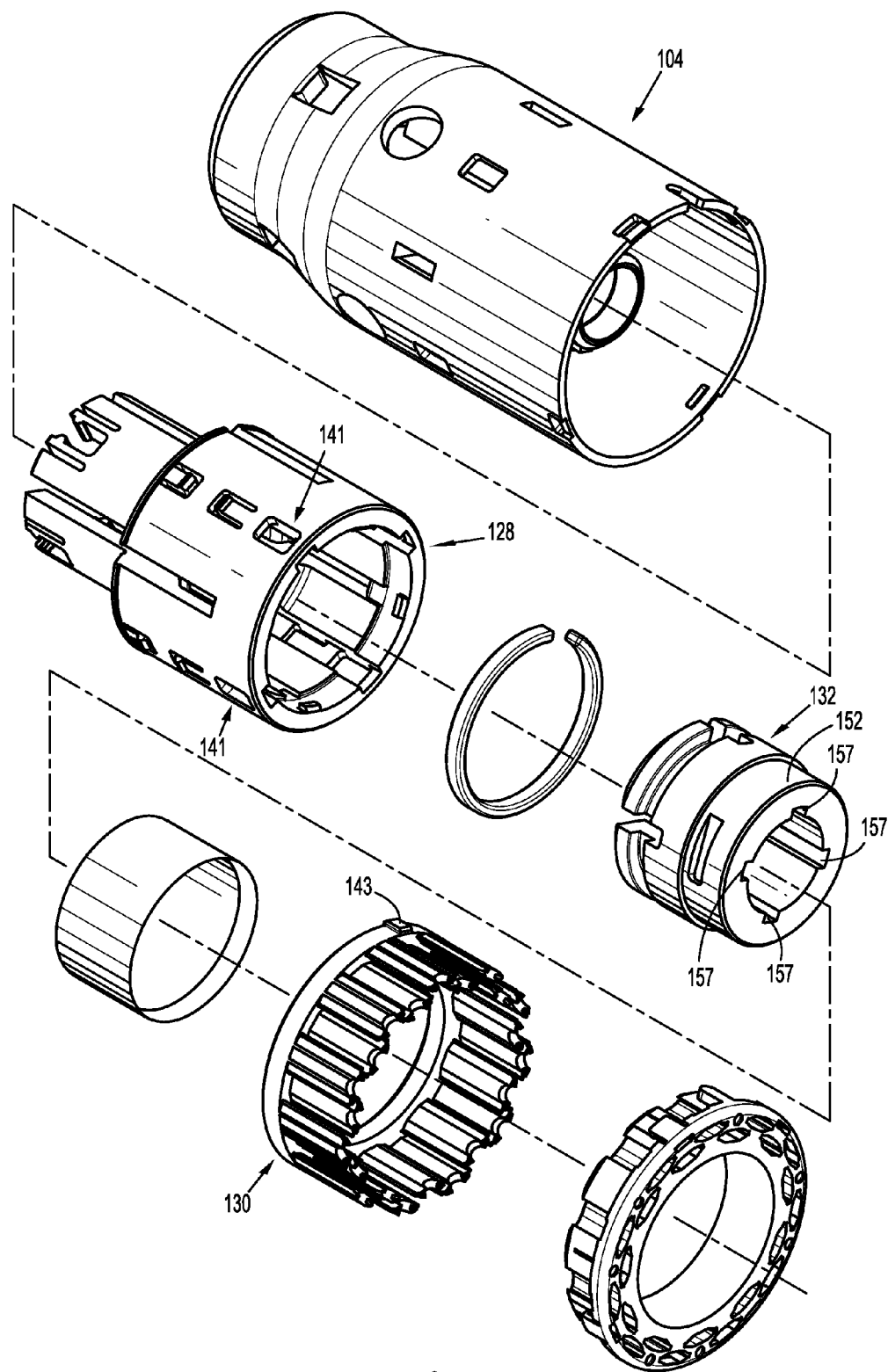
FIG. 7 is an exploded view illustrating components of a shell assembly separated according to another embodiment of the present disclosure.
Figure 8:
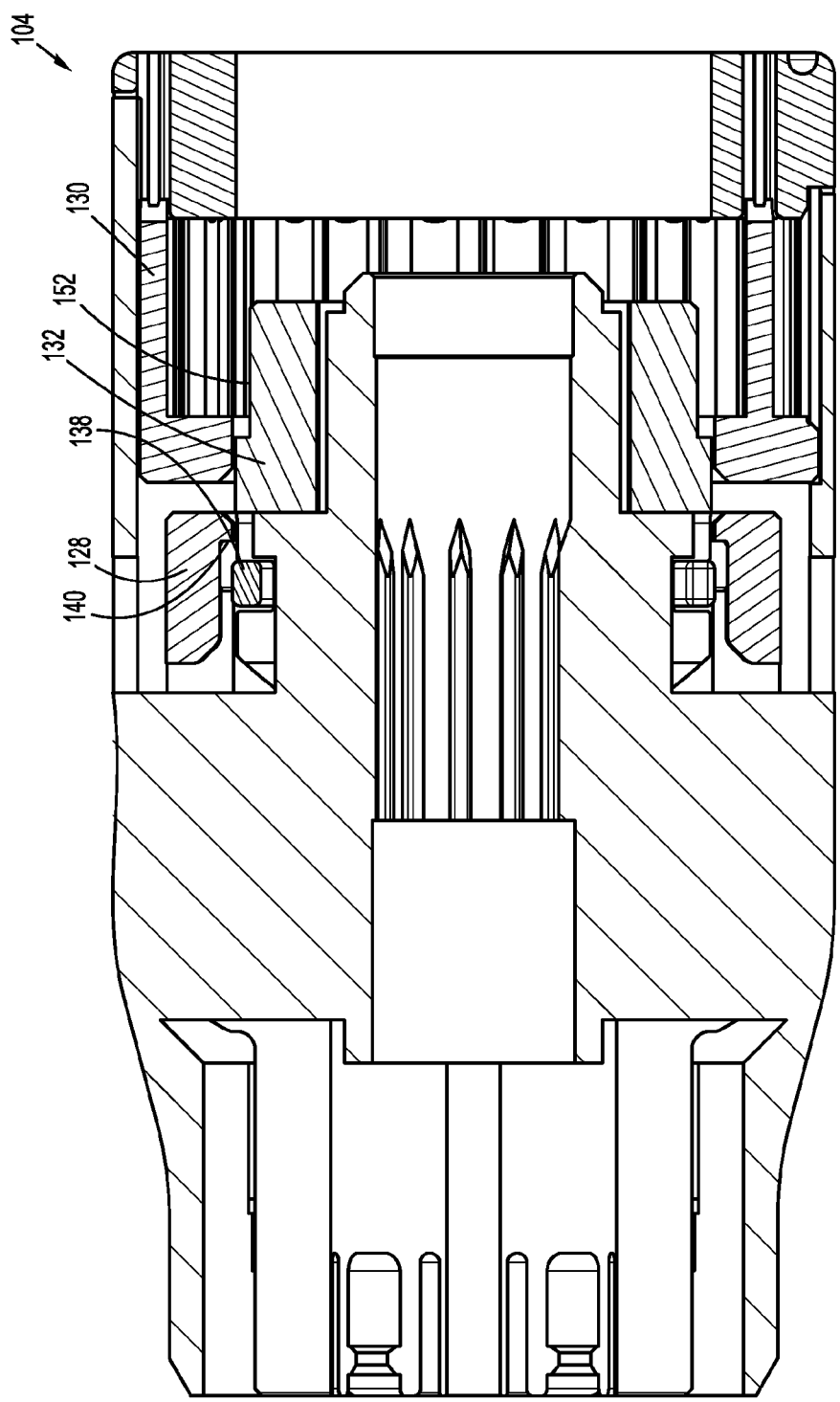
FIGS. 8-9 are side cross-sectional views illustrating positional relationships of the various components of the shell assembly shown in FIG. 7.
Figure 9:
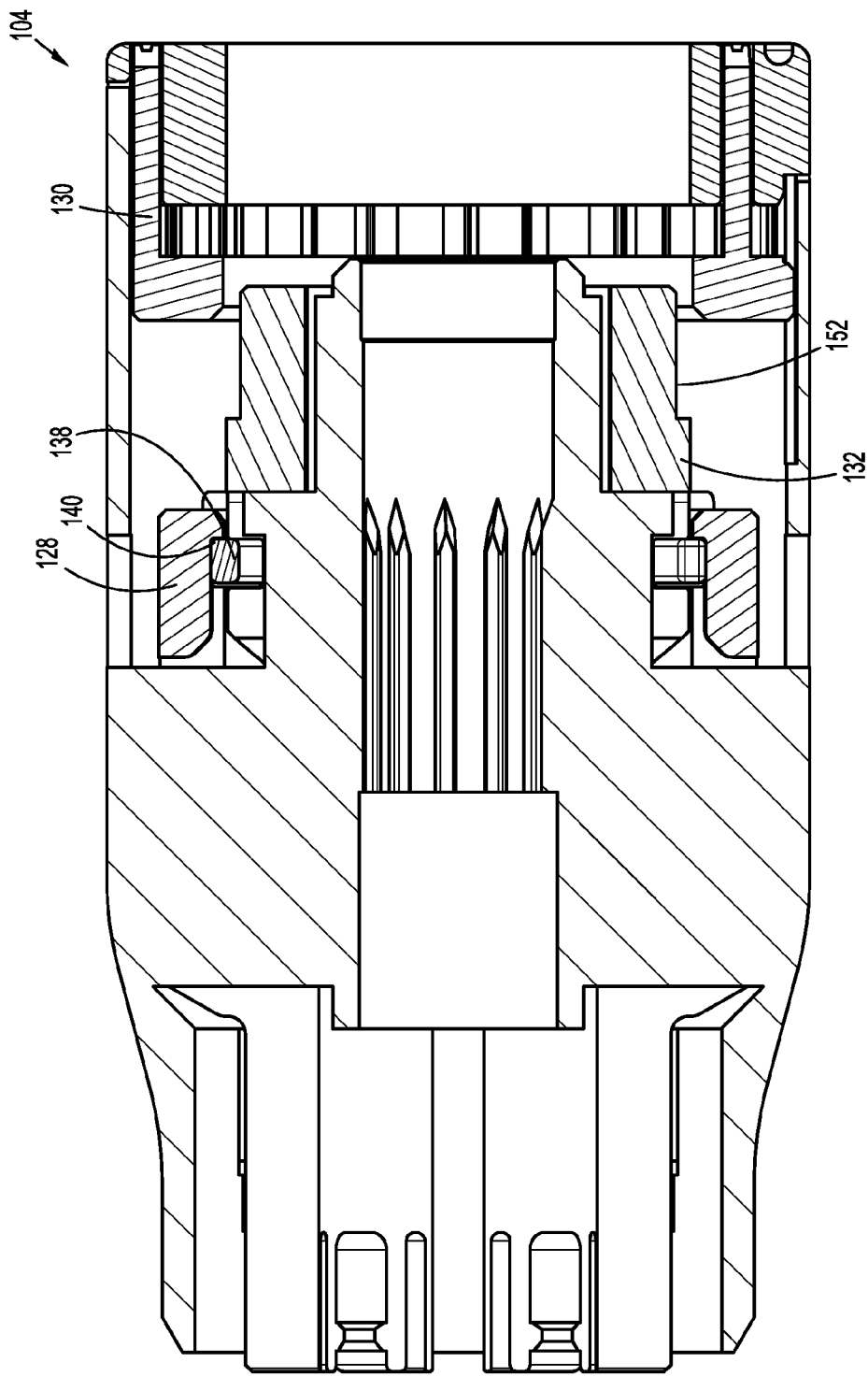

In the embodiment illustrated in FIGS. 7-9, a distal end 152 of the knife pusher 132 includes a plurality of channels 157 (FIG. 7) that extend longitudinally along an interior surface of the knife pusher 132. Channels 157 are configured to keep the knife pusher from rotating when extended. Moreover, unlike main pusher 28, main pusher 128 utilizes an undercut 140 instead of notch 40 (FIGS. 8 and 9) to engage compression member 138.

Operation of the main pusher 128 and the staple pusher 130 are similar to that of the main pusher 28 and the stapler pusher 30, and as such, are not described in detail.

It is contemplated that, in any of the embodiments disclosed herein, the operation of the advancing mechanism, the pusher member, or both, can be utilized to vary the degree to which the staples are deformed or crimped. For example, by approximating the anvil member more closely with the cartridge assembly, the staples are crimped with a relatively smaller internal space and the tissue is compressed to a greater degree. Alternatively, the pusher member can be further advanced, further crimping or deforming the staples. Desirably, there is an indicator on the stapling apparatus handle assembly 6 that allows the surgeon to gauge the degree to which the staples will be crimped. The variable crimp can be used in any of the embodiments disclosed herein, including embodiments in which different sized (pre-formation) staples are used, same sized staples are used, bent or curved backspan staples are used, and/or bent or curved staple forming buckets are used.

The following aspects are also contemplated herein. A replaceable shell assembly 204 (see FIG. 1C, for example) that is configured for use with a circular surgical stapler, may include a main pusher, a staple pusher, and a knife pusher, the main pusher moving the knife pusher independently of the staple pusher, and further including a compressible member supported in the shell assembly and selectively engageable with the knife pusher. In certain embodiments, the compressible member has a compressed configuration and an expanded configuration. In the compressed configuration, the compressible member does not engage the main pusher. In the expanded configuration, the compressible member does engage the knife pusher. In certain embodiments, the main pusher is advanced to advance the pusher member and then retracted to allow the expansion of the compressible member. The main pusher may engage the knife pusher on another advancement of the main pusher. In certain embodiments, the compressible member is biased toward the expanded configuration. In other embodiments, the compressible member is biased toward the compressed configuration.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A circular anastomosis stapler, comprising:
   a handle assembly including a firing trigger actuatable between a first firing stroke and a second firing stroke;
   a shell assembly including a main pusher, a staple pusher and a knife pusher; and
   a compressible member positioned between the main pusher and the knife pusher, the compressible member movable between a first configuration for advancing the staple pusher through the first firing stroke to drive at least one staple from the shell assembly to staple tissue and a second configuration for advancing the knife pusher through the second firing stroke to drive a knife from the shell assembly to core the stapled tissue, wherein the main pusher is retracted subsequent to the first firing stroke and prior to the second firing stroke.

2. A circular anastomosis stapler according to claim 1, wherein the compressible member is a compressible snapring.

3. A circular anastomosis stapler according to claim 1, wherein the shell assembly includes an inner guide portion configured to support the main pusher and knife pusher thereon.

4. A circular anastomosis stapler according to claim 1, wherein the knife pusher includes an annular recess that is configured to support the compressible member therein such that the compressible member can move between the first and second configurations.

5. A circular anastomosis stapler according to claim 1, wherein the main pusher is configured to slide along the compressible member during the first firing stroke to move the staple pusher distally, wherein the main pusher and staple pusher are movable with respect to the knife pusher during the first firing stroke.

6. A circular anastomosis stapler according to claim 1, wherein subsequent to the first firing stroke the main pusher is configured to retract to position a notch defined therein in vertical registration with the compressible member to allow the compressible member to move to the second configuration.

7. A circular anastomosis stapler according to claim 1, wherein the main pusher is configured to slide with the compressible member during the second firing stroke to move the staple pusher and the knife pusher to drive a knife from the shell assembly to core the stapled tissue.

8. A circular anastomosis stapler according to claim 3, wherein at least one protuberance is positioned on the inner guide portion and is configured to selectively engage at least one corresponding recess on the knife pusher such that the compressible member contacts a proximal surface of the protuberance to maintain the knife pusher in a substantially fixed orientation with respect to the inner guide portion when the main pusher is moved through the first firing stroke.

9. A circular anastomosis stapler according to claim 1, wherein the shell assembly is configured to selectively receive an anvil center rod of an anvil assembly of the circular anastomosis stapler.

10. A circular anastomosis stapler, comprising:
- a handle assembly including a firing trigger movable through a first firing stroke and a second firing stroke;
- a shell assembly having a main pusher, a staple pusher and a knife pusher, the staple pusher independently movable with respect to the knife pusher as the main pusher is moved through the first firing stroke; and
- a compressible member supported on the knife pusher and selectively engageable with the main pusher when the main pusher is moved through the second firing stroke, the compressible member transitionable between a compressed configuration for advancing the staple pusher through the first firing stroke to drive at least one staple from the shell assembly to staple tissue and an expanded configuration for advancing the knife pusher through the second firing stroke to drive a knife from the shell assembly to core the stapled tissue.

11. A circular anastomosis stapler according to claim 10, wherein the compressible member is a compressible snap-ring.

12. A circular anastomosis stapler according to claim 10, wherein the shell assembly includes an inner guide portion configured to support the main pusher and knife pusher thereon.

13. A circular anastomosis stapler according to claim 10, wherein the knife pusher includes an annular recess that is configured to support the compressible member therein such that the compressible member can move between the compressed and expanded configurations.

14. A circular anastomosis stapler according to claim 10, wherein the main pusher is configured to slide along the compressible member during the first firing stroke to move the staple pusher distally to drive the at least one staple from the shell assembly to staple tissue.

15. A circular anastomosis stapler according to claim 10, wherein subsequent to the first firing stroke the main pusher is configured to retract to position a notch defined therein in vertical registration with the compressible member to allow the compressible member to move to the expanded configuration.

16. A circular anastomosis stapler according to claim 10, wherein the main pusher is configured to slide with the compressible member during the second firing stroke to move the staple pusher and the knife pusher to drive a knife from the shell assembly to core the stapled tissue.

17. A circular anastomosis stapler according to claim 12, wherein at least one protuberance is positioned on the inner guide portion and is configured to selectively engage at least one corresponding recess on the knife pusher such that the compressible member contacts a proximal surface of the protuberance to maintain the knife pusher in a substantially fixed orientation with respect to the inner guide portion when the main pusher is moved through the first firing stroke.

18. A circular anastomosis stapler according to claim 10, wherein the shell assembly is configured to selectively receive an anvil center rod of an anvil assembly of the circular anastomosis stapler.

19. A shell assembly configured for use with a circular anastomosis stapler, comprising: a main pusher, a staple pusher and a knife pusher, the staple pusher independently movable with respect to the knife pusher as the main pusher is moved through a first firing stroke; and a compressible member supported on the knife pusher and selectively engageable with the main pusher when the main pusher is moved through a second firing stroke, the compressible member transitionable between a compressed configuration for advancing the staple pusher through the first firing stroke to drive at least one staple from the shell assembly to staple tissue and an expanded configuration for advancing the knife pusher through the second firing stroke to drive a knife from the shell assembly to core the stapled tissue.

20. A shell assembly according to claim 19, wherein the compressible member is a compressible snap-ring.

* * * * *